United States Patent

Schneider et al.

[11] Patent Number: 6,037,460
[45] Date of Patent: Mar. 14, 2000

[54] ALKYL 2-ACETAMIDO-2-DEOXYGLUCOPYRANOSIDE URONIC ACIDS AND THEIR PREPARATION

[75] Inventors: Günther Schneider, Hamburg; Hartmut Schmidt-Lewerkühne, Schenefeld; Joachim Thiem; Oliver Scheel, both of Hamburg, all of Germany

[73] Assignee: Beiersdorf AG, Hamburg, Germany

[21] Appl. No.: 08/840,002

[22] Filed: Apr. 24, 1997

[30] Foreign Application Priority Data

Apr. 27, 1996 [DE] Germany ............... 196 17 019

[51] Int. Cl.[7] .............. C07H 15/04; C07H 1/08; C07H 7/033; B01F 17/56
[52] U.S. Cl. .............. 536/17.2; 536/18.6; 536/124; 514/25; 514/42; 516/27; 516/69; 516/915
[58] Field of Search .............. 536/20, 22.1, 29.1, 536/17.3, 18.6, 4.1, 17.2, 124; 514/42, 822, 25; 252/357; 516/27, 69, 915

[56] References Cited

U.S. PATENT DOCUMENTS

| | | | |
|---|---|---|---|
| 2,662,073 | 12/1953 | Mehltretter et al. | 252/357 |
| 2,783,148 | 2/1957 | Gyorgy et al. | 536/20 |
| 2,959,583 | 11/1960 | Doczi | 536/20 |
| 4,533,549 | 8/1985 | Lasker | 514/822 |
| 4,987,223 | 1/1991 | Choay et al. | 536/18.6 |
| 5,312,907 | 5/1994 | Schattschneider et al. | 536/18.6 |
| 5,539,091 | 7/1996 | El Ghoul et al. | 536/22.1 |
| 5,696,246 | 12/1997 | Schmidt et al. | 536/18.6 |
| 5,773,608 | 6/1998 | Yen et al. | 536/20 |

FOREIGN PATENT DOCUMENTS

| | | |
|---|---|---|
| 2717176 | 9/1995 | France . |
| WO 93 04662 | 3/1993 | WIPO . |

OTHER PUBLICATIONS

Yoshikawa et al., Chemical Transformation of Uronic Acids leading to Aminocyclitols. IV. Synthesis of Hexaacetyl-streptamine from N-Acetyl-D-glucosamine by Means of Electrolytic Decarboxylation, Chem Pharm Bull, 29(9) 2582–2586 (Sep. 9, 1981).

*Primary Examiner*—D. Gabrielle Brouillette
*Assistant Examiner*—Daniel S. Metzmaier
*Attorney, Agent, or Firm*—Norris McLaughlin & Marcus

[57] ABSTRACT

Alkyl 2-acetamido-2-deoxy-D-glucopyranoside uronic acids, and their pharmaceutically or cosmetically acceptable salts, and their use as surface-active and/or interfacially active active compounds, in particular as detergent surfactants or emulsifiers.

9 Claims, No Drawings

ALKYL 2-ACETAMIDO-2-DEOXYGLUCOPYRANOSIDE URONIC ACIDS AND THEIR PREPARATION

The present invention relates to novel active compounds, their preparation and their use in the field of cosmetic and of pharmaceutical dermatology. In particular, the present invention relates to active compounds and cosmetic and dermatological preparations comprising such active compound combinations. In particular, the present invention relates to active compounds which have surfactant properties. The invention further relates to cosmetic and dermatological preparations which contain such substances. In a preferred embodiment, the present invention relates to cosmetic cleansing agents.

Agents of this type are known per se. In this context, they are essentially surface-active substances or substance mixtures which are offered to the consumer in various preparations.

Preparations of this type are, for example, bubble baths and shower baths, solid and liquid soaps or so-called "syndets" (synthetic detergents), shampoos, hand-washing pastes, intimate cleansing agents, special cleansing agents for infants and the like.

Surface-active substances—the best-known of which are the alkali metal salts of the higher fatty acids, i.e. the classical "soaps"—are amphiphilic substances which can emulsify, organic non-polar substances in water.

These substances wash not only dirt from the skin and hair; depending on the choice of the surfactant or of the surfactant mixture, they irritate the skin and mucous membranes to a greater or lesser degree. The most useful surfactant for cosmetic cleansing agents is sodium lauryl ether sulphate. Although it has good washing power and—depending on dosage—is very highly skin—and mucous membrane-tolerable, sensitive persons should avoid frequent contact with it.

There are admittedly a large number of very mild surfactants available, but the surfactants of the prior art are either mild, but cleanse poorly, or else they cleanse well, but irritate the skin or mucous membranes.

Cosmetic emulsions also contain interfacially active substances, so-called emulsifiers. These reduce the surfaces of contact between the phases and form oil/water interfacial films on the phase boundary. As a result, the irreversible confluence of the dispersed phase is counteracted.

Efficient emulsifiers are therefore distinguished by a very good emulsifying, solubilizing and dispersing ability. To a great extent, it is desirable that such substances do not cause skin irritation. The choice of such substances known to the prior art is restricted. it was therefore an object of the present invention to enrich the prior art in this respect.

Advantageous cleansing formulations, even within the meaning of the present invention, are shower preparations.

Preparations of this type are known per se. In this context, they are essentially surface-active substances or substance mixtures which are offered to the consumer in various preparations. Preparations of such a type are in general distinguished by a high water content to a greater or lesser degree, but can also be present, for example, as a concentrate.

In general, preparations which are intended for the shower bath do not differ or hardly differ from bath preparations apart from the fact that in the case of shower preparations products of higher viscosity are preferred, which do not run from the hand after removal from the container. In the case of bath preparations, this is less of practical importance.

Even in the case of a simple water bath without addition of surfactants, a swelling of the horny layer of the skin first occurs, the degree of this swelling, for example, depending on the duration of the bath and its temperature. At the same time, water-soluble substances, e.g. water-soluble dirt constituents, but also substances endogenous to the skin, which are responsible for the water-binding power of the horny layer, are washed off or washed out. As a result of surface-active substances endogenous to the skin, skin oils are additionally also dissolved to a certain extent and washed out. After initial swelling, this causes a subsequent marked drying out of the skin, which can be increased by detergent additives.

In healthy skin, these processes are in general unimportant, as the protective mechanisms of the skin can compensate for such slight disturbances of the upper skin layers without problem. However, even in the case of non-pathological variations from the normal status, e.g. as a result of environmentally related wear and tear and irritations, damage due to light, presbyderma, etc., the protective mechanism of the skin surface is disturbed. Under certain circumstances, it is then no longer able by itself to fulfil its objects and must be regenerated by external measures.

The prior art is acquainted with oil bath preparations of various types, it being possible to vary the properties of the fat or oil phase by addition of surface-active substances. In this case, depending on the nature and amount of the constituents chosen, preparations can be formulated which either produce spreading oil films, oil-in-water systems or even total solubilizates on the bath-water surface. Foaming formulations, but also only slightly foaming or non-foaming formulations, are possible. In general, the functionality of preparations of this type is restricted in oil bath or oil cream bath preparations to the refatting or superfatting of the uppermost layers of skin.

Nevertheless, caring oils can in isolated cases at best cover up the harmful effect of a not very skin-friendly surfactant, which is why an oil bath or an oil cream bath cannot be better than the surfactant(s) employed therein.

It was thus the object of the present invention to remedy the defects of the prior art in this respect.

In a further preferred embodiment, the present invention relates to cosmetic and dermatological preparations for the prophylaxis and treatment of cosmetic or dermatological cell changes, in particular skin changes such as, for example, skin ageing, in particular the cell ageing caused by oxidative processes, in particular skin ageing.

Finally, it was an object of the present invention to conceive preparation processes for such active compounds.

It was surprising and not to be foreseen by the person skilled in the art that alkyl 2-acetamido-2-deoxy-D-glucopyranoside uronic acids of the general formula

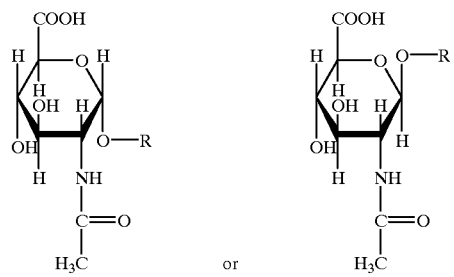

where R is representative of the group consisting of branched and unbranched alkyl of 1–48 C atoms, in particular of 14–22, preferably 16–18, C atoms, and their salts, and a process for the preparation of alkyl 2-acetamido-2-deoxy-D-glucopyranoside uronic acids of the general formula

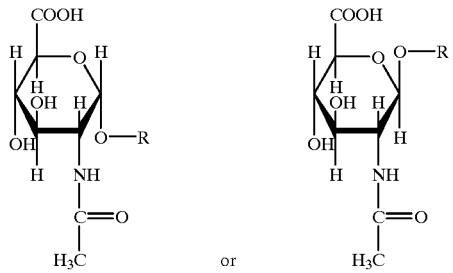 or where R is representative of the group consisting of branched and unbranched alkyl of 1–48 C atoms, in particular of 14–22, preferably 16–18, C atoms, and their salts, characterized in that (1) chitin is ground (2) the ground chitin is treated with acid and a first aliphatic alcohol of low chain length, preferably of a chain length of less than $C_8$, whereupon (3) if desired the reaction product thus obtained is purified by dialysis, preferably electrodialysis, (4) a second alcohol not identical to the first aliphatic alcohol, preferably of a chain length of $C_8$ and longer, is reacted with the reaction product under acid catalysis, whereby the first aliphatic alcohol becomes free again and (4a) if desired is removed by distillation, (5) the reaction product is subjected to oxidation, and the alkyl 2-acetamido-2-deoxy-D-glucopyranoside uronic acids or their salts obtained in this process and the novel intermediates in this process eliminate all outlined disadvantages of the prior art.

Consequently, also according to the invention is the use of alkyl 2-acetamido-2-deoxy-D-glucopyranaside uronic acids of the general formula

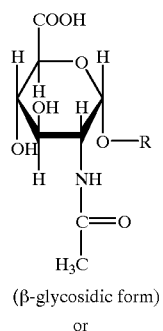

(β-glycosidic form)

or

-continued

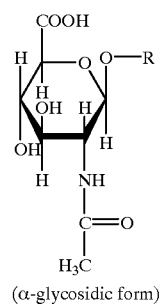

(α-glycosidic form)

where R is representative of the group consisting of branched and unbranched alkyl of 1–48 C atoms, in particular of 14–22, preferably 16–18, C atoms, as surface-active and/or interfacially active active compounds, in particular as detergent surfactants or emulsifiers, and where the uronic acids can preferably be present in the form of their salts, in particular as alkali metal salts, of these preferably the sodium salt, or as ammonium, alkylammonium, dialkylammonium, trialkylammonium or tetraalkylammonium salts.

The substances obtained according to the invention are distinguished by outstanding skin-friendliness, very good surface-active and interfacially active activity and processability in cosmetic and dermatological preparations.

Mixtures of α- and β-glycosides can also be advantageous according to the invention. In any case, a plethora of processes which are able to separate the anomers are known to the person skilled in the art, for example chromatographic processes.

The alkyl 2-acetamido-2-deoxy-D-glucopyranoside uronic acids and their advantageous salts according to the invention are derived formally as well as practically from chitin, which is characterized by the structural formula

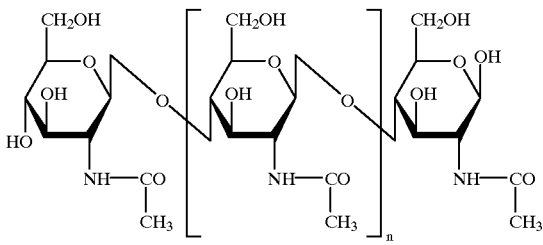

Chitin is an essential constituent of the exoskeleton ['οχιτων=Grk.: armoured jacket] of the arthropods (e.g. insects, crabs, spiders) and is also found in supportive tissues of other organisms (e.g. molluscs, algae, fungi)

The use of chitin derivatives, namely of chitosan, a hydrolysis product of chitin, in cosmetic preparations is known per se. Chitosan, for example, is better suited than the chitin on which it is based, as a thickener or stabilizer and improves the adhesion and water-resistance of polymeric films. Representing a multiplicity of places where this is found in the prior art: H. P. Fiedler, "Lexikon der Hilfstoffe für Pharmazie, Kosmetik und angrenzende Gebiete" [Encyclopedia of auxiliaries for pharmacy, cosmetics and neighbouring fields], 4th Edition 1989, Editio Cantor, Aulendorf, p. 349, headword "Chitosan".

The use of other sugar derivatives as surface-active substances in cosmetics, dermatics and other preparations has also been thoroughly disclosed, for example in the Patent Application Documents WO 93/07249, German Offenlegungsschrift 41 29 124, German Offenlegungsschrift 41 02 502, German Offenlegungsschrift 40 26 471 and German Offenlegungsschrift 40 26 809.

Nevertheless, it was not possible for the prior art to make any hint at the present invention.

According to the invention, a process is advantageously used which is modelled on the following reaction scheme:

It is furthermore advantageous (5) to subject the reaction product to oxidation with $Pt/O_2$ (Adam's catalyst).

According to the invention, an anomer mixture is obtainable which can be separated into the anomers by methods familiar to the person skilled in the art. According to the invention, mainly the α-anomer is obtained, usually in a nine-fold excess compared with the β-anomer.

It can also be advantageous to start from commercially available alkyl 2-acetamido-2-deoxyglucopyranosides and

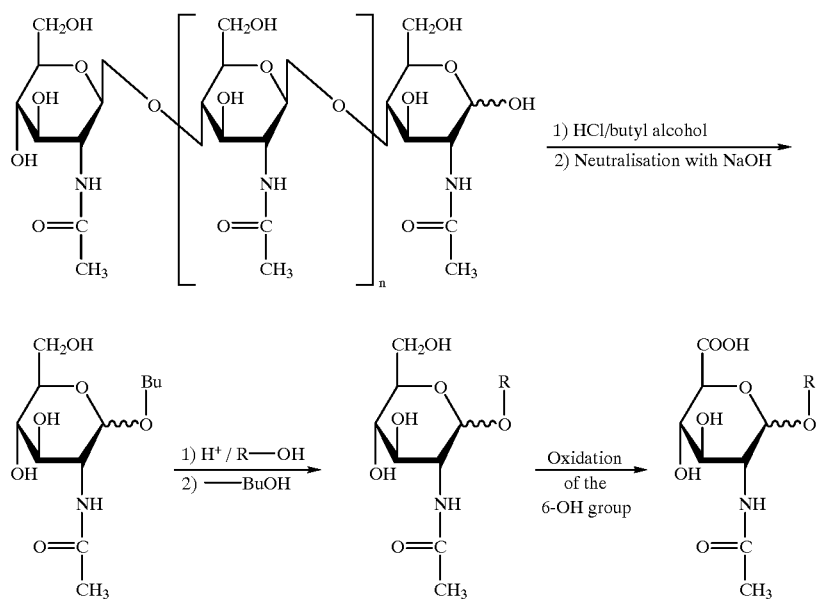

Particularly advantageous reaction conditions provide that (2) the ground chitin is treated in the presence of heat, advantageously at temperatures of 40–70° C., in particular about 55° C., with acid and a first aliphatic alcohol.

Particularly advantageous reaction conditions provide that (4) a second alcohol not identical to the first aliphatic alcohol, preferably of a chain length of $C_8$ and longer, is reacted with the reaction product under acid catalysis, as a result of which the first aliphatic alcohol becomes free again and (4a) is removed in vacuo by distillation.

A suitable temperature range for this reaction step and for the distillative removal of the first aliphatic alcohol is between 80 and 100° C., preferably about 90° C.

The acid catalysis can be carried out on acidic ion-exchange resins, e.g. Amberlite IR 120, by means of camphorsulphonic acid or hydrochloric acid.

At the end of this reaction step, a neutralisation can advantageously be carried out, e.g. using sodium hydroxide solution or on basic ion-exchange resins.

only to carry out the reaction step (5) according to the reaction scheme

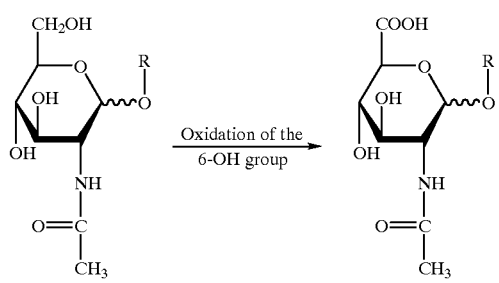

It has further emerged that the alkyl 2-acetamido-2-deoxyglucopyranosides which are known per se are also outstandingly suitable as surface-active or interfacially active substances. Therefore, also according to the invention is the use of alkyl 2-acetamido-2-deoxyglucopyranosides of the general structural formula

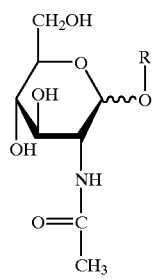

where R is representative of the group consisting of branched and unbranched alkyl of 1–48 C atoms, in particular of 14–22, preferably 16–18, C atoms, as surface-active and/or interfacially active active compounds, in particular as detergent surfactants or emulsifiers.

The cosmetic or dermatological formulations according to the invention can be made up in the customary manner and used for the treatment, the care and the cleansing of the skin and/or the hair and as a make-up product in decorative cosmetics. They preferably contain 0.001% by weight to 10% by weight, but in particular 0.01% by weight to 6% by weight, based on the total weight of the composition, of the alkyl 2-acetamido-2-deoxy-D-glucopyranoside uronic acids according to the invention.

For use, the cosmetic and dermatological preparations according to the invention are applied to the skin and/or the hair in adequate amounts in the manner customary for cosmetics.

Cosmetic and dermatological preparations according to the invention can be present in various forms. Thus it is possible to prepare, for example, a solution, an anhydrous preparation, an emulsion or microemulsion of the type water-in-oil (W/O) or of the type oil-in-water (O/W), a multiple emulsion, for example of the type water-in-oil-in-water (W/O/W), a gel, a solid stick, an ointment or alternatively an aerosol.

It is also possible and advantageous within the meaning of the present invention to add the alkyl 2-acetamido-2-deoxy-D-glucopyranoside uronic acids according to the invention to aqueous systems or surfactant preparations for cleansing the skin and the hair.

The cosmetic and dermatological preparations according to the invention can contain cosmetic auxiliaries, such as are customarily used in such preparations, e.g. preservatives, bactericides, perfumes, substances for preventing foaming, colourants, pigments which have a colouring action, thickening agents, surface-active substances, emulsifiers, emollient, moisturizing and/or moisture-retaining substances, fats, oils, waxes or other customary constituents of a cosmetic or dermatological formulation such as alcohols, polyols, polymers, foam stabilizers, electrolytes, organic solvents or silicone derivatives.

In particular, the alkyl 2-acetamido-2-deoxy-D-glucopyranoside uronic acids can also be combined with antioxidants.

According to the invention, convenient antioxidants which can be used are all antioxidants suitable or customary for cosmetic and/or dermatological applications.

Advantageously, the antioxidants are selected from the group consisting of amino acids (e.g. glycine, histidine, tyrosine, tryptophan) and their derivatives, imidazoles (e.g. urocaninic acid) and their derivatives, peptides such as D,L-carnosine, D-carnosine, L-carnosine and their derivatives (e.g. anserine), carotenoids, carotenes (e.g. α-carotene, β-carotene, lycopene) and their derivatives, chlorogenic acid and its derivatives, lipoic acid and its derivatives (e.g. dihydrolipoic acid), aurothioglucose, propylthiouracil and other thiols (e.g. thioredoxin, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and also their salts, dilauryl thiodipropionate, distearyl thiodipropionate, thiodipropionic acid and its derivatives (esters, ethers, peptides, lipids, nucleotides, nucleosides and salts) as well as sulphoximine compounds (e.g. buthionine sulphoximine, homocystein sulphoximine, buthionine sulphone, penta-, hexa and heptathionine sulphoximine) in very low tolerable doses (e.g. pmol to µmol/kg), furthermore (metal) chelators (e.g. α-hydroxy fatty acids, palmitic acid, phytic acid, lactoferrin), α-hydroxy acids (e.g. citric acid, lactic acid, maleic acid), humic acid, bile acid, bile extracts, bilirubin, biliverdin, EDTA, EGTA and their derivatives, unsaturated fatty acids and their derivatives (e.g. γ-linolenic acid, linoleic acid, oleic acid), folic acid and its derivatives, ubiquinone and ubiquinol and their derivatives, vitamin C and derivatives (e.g. ascorbyl palmitate, Mg-ascorbyl phosphate, ascorbyl acetate), tocopherols and derivatives (e.g. vitamin E acetate), vitamin A and derivatives (vitamin A palmitate) as well as coniferyl benzoate of benzoin, rutic acid and its derivatives, α-glycosylrutin, ferulic acid, furfurylidenglucitol, carnosine, butylhydroxytoluene, butylhydroxyanisole, nordihydroguairetic acid, trihydroxybutyrophenone, uric acid and its derivatives, mannose and its derivatives, zinc and its derivatives (e.g. ZnO, $ZnSO_4$), selenium and its derivatives (e.g. selenomethionine), stilbenes and their derivatives (e.g. stilbene oxide, trans-stilbene oxide) and the suitable derivatives according to the invention (salts, esters, ethers, sugars, nucleotides, nucleosides, peptides and lipids) of these mentioned active compounds.

The amount of the abovementioned antioxidants (one or more compounds) in the preparations is preferably 0.001 to 300% by weight, particularly preferably 0.05–20% by weight, in particular 1–10% by weight, based on the total weight of the preparation.

If vitamin E and/or its derivatives are the antioxidant(s), it is advantageous to select their respective concentrations from the range from 0.001–10% by weight, based on the total weight of the formulation.

If vitamin A, or vitamin A derivatives, or carotenes or their derivatives are the antioxidant(s) it is advantageous to select their respective concentrations from the range from 0.001–100% by weight, based on the total weight of the formulation.

Emulsions according to the invention are advantageous and contain, for example, the fats, oils, waxes and other fatty materials mentioned, as well as water and an emulsifier, such as is customarily used for such a type of formulation.

The lipid phase can in this case advantageously be selected from the following substance group:

natural, synthetic and/or partially synthetic oils, such as triglycerides of capric or of caprylic acid, but preferably castor oil;

fats, waxes and other natural synthetic and/or partially synthetic fatty materials, preferably esters of fatty acids with alcohols of low C number, e.g. with isopropanol, propylene glycol or glycerol, or esters of fatty alcohols with alkanoic acids of low C number or with fatty acids;

silicone oils such as dimethylpolysiloxanes, diethylpolysiloxanes, diphenylpolysiloxanes as well as mixed forms thereof;

saturated compounds such as hydrocarbons of natural or synthetic origin (petroleum jelly, squalane).

The aqueous phase of the preparations according to the invention if desired advantageously contains alcohols, diols or polyols of low C number, as well as their ethers, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products and also, in particular, one or more thickening agents, which can advantageously be selected from the group consisting of silica, aluminium silicates, polysaccharides and their derivatives, e.g. hyaluronic acid, xanthan gum, hydroxypropylmethylcellulose, particularly advantageously from the group consisting of the polyacrylates, preferably a polyacrylate from the group consisting of the so-called carbopols, for example carbopols of the types 980, 981, 1382, 2984, 5984, in each case individually or in combination.

In particular, mixtures of the abovementioned solvents are used. In the case of alcoholic solvents water can be a further constituent.

Gels according to the invention customarily contain alcohols of low C number, e.g. ethanol, isopropanol, 1,2-propanediol, glycerol and water or an above-mentioned oil in the presence of a thickening agent which in the case of oily-alcoholic gels is preferably silica or an aluminium silicate, and in the case of aqueous-alcoholic or alcoholic gels preferably a polyacrylate.

Suitable propellants for preparations according to the invention which can be sprayed from aerosol containers are the customary known easily volatile, liquefied propellants, for example hydrocarbons (propane, butane, isobutane), which can be employed on their own or as a mixture with one another. Compressed air can also advantageously be used.

Advantageously, preparations according to the invention can additionally contain substances which absorb UV radiation in the UVB range, the total amount of the filter substances being, for example, 0.1% by weight to 30% by weight, preferably 0.5 to 10% by weight, in particular 1.0 to 6.0% by weight, based on the total weight of the preparations, in order to make available cosmetic preparations which protect the hair or the skin from the entire range of ultraviolet radiation. They can also be used as sunscreens for the hair or the skin.

If the emulsions according to the invention contain UVB filter substances, these can be oil-soluble or water-soluble. Advantageous oil-soluble UVB filters according to the invention are, for example:

3-benzylidencamphor derivatives, preferably 3-(4-methylbenzylidene)camphor, 3-benzylidenecamphor;

4-aminobenzoic acid derivatives, preferably 2-ethylhexyl 4-dimethylaminobenzoate, amyl 4-dimethylaminobenzoate;

esters of cinnamic acid, preferably 2-ethylhexyl 4-methoxycinnamate, isopentyl 4-methoxycinnamate;

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzylidenemalonic acid, preferably di(2-ethylhexyl) 4-methoxybenzylidenemalonate, 2,4,6-trianilino-(p-carbo-2'-ethyl-1'-hexyloxy)-1,3,5-triazine.

Advantageous water-soluble UVB filters are, for example:

salts of 2-phenylbenzimidazole-5-sulphonic acid such as its sodium, potassium or its triethanolammonium salt, as well as the sulphonic acid itself;

sulphonic acid derivatives of benzophenone, preferably 2-hydroxy-4-methoxybenzophenone-5-sulphonic acid and its salts;

sulphonic acid derivatives of 3-benzylidenecamphor, such as, for example, 4-(2-oxo-3-bornylidenemethyl)-benzenesulphonic acid, 2-methyl-5-(2-oxo-3-bornylidenemethyl)sulphonic acid and their salts.

The list of the UVB filters mentioned, which can be used in combination with the alkyl 2-acetamido-2-deoxy-D-glucopyranoside uronic acids according to the invention, should of course be non-limiting.

The invention also relates to the use of a combination of the alkyl 2-acetamido-2-deoxy-D-glucopyranoside uronic acids according to the invention with at least one UVB filter as antioxidant or the use of a combination of the tocopherylglycosides according to the invention with at least one UVB filter as antioxidant in a cosmetic or dermatological preparation.

It can also be advantageous to combine alkyl 2-acetamido-2-deoxy-D-glucopyranoside uronic acids according to the invention with UVA filters which to date are customarily contained in cosmetic preparations. These substances are preferably derivatives of dibenzoylmethane, in particular 1-(4'-tert-butylphenyl)-3-(4'-methoxyphenyl) propane-1,3-dione and 1-phenyl-3-(4'-isopropylphenyl) propane-1,3-dione. These combinations and preparations which contain these combinations are also a subject of the invention. The amounts used for the UVB combination can be employed.

The invention also relates to the use of a combination of the alkyl 2-acetamido-2-deoxy-D-glucopyranoside uronic acids according to the invention with at least one UVA filter as antioxidant or the use of a combination of the tocopherylglycosides according to the invention with at least one UVA filter as antioxidant in a cosmetic or dermatological preparation.

The invention also relates to the use of a combination of the alkyl 2-acetamido-2-deoxy-D-glucopyranoside uronic acids according to the invention with at least one UVA filter and at least one UVB filter as antioxidant or the use of a combination of the tocopherylglycosides according to the invention with at least one UVA filter and at least one UVB filter as antioxidant in a cosmetic or dermatological preparation.

Cosmetic and dermatological preparations having an efficacious content of alkyl 2-acetamido-2-deoxy-D-glucopyranoside uronic acids according to the invention can also contain inorganic pigments which are customarily used in cosmetics for the protection of the skin from UV rays. In this case, these are oxides of titanium, zinc, iron, zirconium, silicon, manganese, aluminium, cerium and mixtures thereof, as well as modifications in which the oxides are the active agents. Particularly preferably, they are pigments based on titanium dioxide.

These combinations of UVA filter and pigment or preparations which contain this combination are also a subject of the invention. The amounts mentioned for the above combinations can be used.

Cosmetic and dermatological preparations for the protection of the hair from UV rays according to the invention are, for example, shampoos, preparations which are applied when rinsing the hair before or after shampooing, before or after permanent wave treatment, or before or after dyeing or bleaching hair, preparations for hot-air drying or setting of the hair, preparations for dyeing or bleaching, a hairdressing and treatment lotion, a hair lacquer or permanent wave compositions.

The cosmetic and dermatological preparations contain active compounds and auxiliaries, such as are customarily used for this type of preparations for hair care and hair treatment. Auxiliaries used are preservatives, surface-active substances, substances for preventing foaming, thickening agents, emulsifiers, fats, oils, waxes, organic solvents, bactericides, perfumes, dyes or pigments whose object is to colour the hair or the cosmetic or dermatological preparation itself, electrolytes and substances preventing the hair from becoming greasy.

Electrolytes within the meaning of the present invention are water-soluble alkali metal, ammonium, alkaline earth metal (including magnesium) and zinc salts of inorganic anions and any desired mixtures of those salts, where it must be guaranteed that these salts are distinguished by pharmaceutical or cosmetic acceptability.

The anions according to the invention are preferably selected from the group consisting of the chlorides, the sulphates and hydrogen sulphates, the phosphates, hydrogen phosphates and the linear and cyclic oligophosphates as well as the carbonates and hydrogen carbonates.

Cosmetic preparations which are a skin-cleansing agent or shampoo preferably contain at least one further anionic, non-ionic or amphoteric and surface-active substance or surface-active betaines, or alternatively mixtures of such substances, furthermore alkyl 2-acetamido-2-deoxy-D-glucopyranoside uronic acids according to the invention in aqueous medium and auxiliaries, such as are customarily used for this purpose. The surface-active substance or the mixtures of these substances can be present in a concentration of between 1% by weight and 50% by weight in the shampoo.

If the cosmetic or dermatological preparations are present in the form of a lotion which is rinsed out and is applied, for example, before or after bleaching, before or after shampooing, between two shampooing steps, or before or after permanent wave treatment, they are in this case, for example, aqueous or aqueous-alcoholic solutions which optionally contain surface-active substances whose concentration can be between 0.1 and 10% by weight, preferably between 0.2 and 5% by weight.

These cosmetic or dermatological preparations can also be aerosols containing the auxiliaries customarily used for this purpose.

A cosmetic preparation in the form of a lotion which is not rinsed out, in particular a lotion for setting the hair, a lotion which is used during hot-air drying of the hair, or a hairdressing and treatment lotion, is in general an aqueous, alcoholic or aqueous-alcoholic solution and contains at least one cationic, anionic, non-ionic or amphoteric polymer or alternatively mixtures thereof, as well as active compound combinations according to the invention in an efficacious concentration. The amount of the polymers used is, for example, between 0.1 and 10% by weight, preferably between 0.1 and 3% by weight.

Cosmetic preparations for the treatment and care of the skin and of the hair, which contain alkyl 2-acetamido-2-deoxy-D-glucopyranoside uronic acids according to the invention can be present as emulsions which are of the non-ionic or cationic type. Besides water, non-ionic emulsions contain oils or fatty alcohols which, for example, can also be polyethoxylated or polypropoxylated, or alternatively mixtures of both organic components. These emulsions optionally contain cationic surface-active substances.

According to the invention, cosmetic preparations for the treatment and care of the hair can also be present as gels which, besides an efficacious content of alkyl 2-acetamido-2-deoxy-D-glucopyranoside uronic acids according to the invention, preferably contain water, further organic thickening agents, e.g. gum arabic, xanthan gum, sodium alginate, cellulose derivatives, preferably methylcellulose, hydroxymethylcellulose, hydroxyethylcellulose, hydroxypropylcellulose, hydroxypropylmethylcellulose or inorganic thickening agents, e.g. aluminium silicates such as, for example, bentonites, or a mixture of polyethylene glycol and polyethylene glycol stearate or distearate. The thickening agent is contained in the gel, for example, in an amount of between 0.1 and 30% by weight, preferably of between 0.5 and 15% by weight.

Preferably, the amount of the alkyl 2-acetamido-2-deoxy-D-glucopyranoside uronic acids according to the invention in a composition intended for the hair is 0.05% by weight to 10% by weight, in particular 0.5% by weight to 5% by weight, based on the total weight of the composition.

Aqueous cosmetic cleansing agents according to the invention or cleansing agent concentrates which are low in water or water-free intended for aqueous cleansing can contain anionic, non-ionic and/or amphoteric surfactants, for example conventional soaps, e.g. fatty acid salts of sodium, alkyl sulphates, alkyl ether sulphates, alkane- and alkylbenzenesulphonates, sulphoacetates, sulphobetaines, sarcosinates, amidosulphobetaines, sulphosuccinates, sulphosuccinic acid monoesters, alkyl ether carboxylates, protein-fatty acid condensates, alkylbetaines and amidobetaines, fatty acids alkanolamides and/or polyglycol ether derivatives.

Cosmetic preparations which are cosmetic cleansing preparations for the skin can be present in liquid or solid form. Besides the alkyl 2-acetamido-2-deoxy-D-glucopyranoside uronic acids according to the invention or their salts, they can preferably contain at least one anionic, non-ionic or amphoteric surface-active substance or mixtures thereof, and if desired one or more electrolytes and auxiliaries, such as are customarily used for this purpose. The surface-active substance can be present in a concentration of between 1 and 94% by weight in the cleansing preparations, based on the total weight of the preparations.

Besides an efficacious content of alkyl 2-acetamido-2-deoxy-D-glucopyranoside uronic acids according to the invention or their salts, cosmetic preparations which are a shampoo preferably contain at least one anionic, non-ionic or amphoteric surface-active substance or mixtures thereof, and if desired an electrolyte and auxiliary according to the invention, such as are customarily used for this purpose. The surface-active substance can be present in a concentration of between 1% by weight and 94% by weight in the shampoo.

Apart from the abovementioned surfactants, the compositions according to the invention contain water and, if desired, the additives customary in cosmetics, for example perfume, thickener, colourants, antimicrobial substances, refatting agents, complexing and sequestering agents, pearl lustre agents, plant extracts, vitamins, active compounds and the like.

Preferably, the amount of alkyl 2-acetamido-2-deoxy-D-glucopyranoside uronic acids used according to the invention in these preparations is 0.001% by weight to 10% by weight, in particular 0.1% by weight to 3% by weight, based on the total weight of the preparations.

The invention also relates to the process for the preparation of the cosmetic compositions according to the invention, which is characterized in that alkyl 2-acetamido-2-deoxy-D-glucopyranoside uronic acids are incorporated into cosmetic and dermatological formulations in a manner known per se.

The following examples are intended to explain the present invention without restricting it.

PREPARATION EXAMPLE 1

Stearyl 2-acetamido-2-deoxy-D-glucopyranoside Uranic Acid Na Salt

Ground chitin is treated at 55° C. with hydrochloric acid and butyl alcohol and the reaction product thus obtained is purified by electrodialysis. The reaction product is reacted with stearyl alcohol with acid catalysis with camphorsulphonic acid at 90° C. and the butyl alcohol is stripped off under a water-jet vacuum at 90° C. The product is neutralized with NaOH and the product is oxidized to the final product at 60° C. using Adam's catalyst.

PREPARATION EXAMPLE 2

Cetyl 2-acetamido-2-deoxy-D-glucopyranoside Uranic Acid Na Salt

Ground chitin is treated at 55° C. with hydrochloric acid and butyl alcohol and the reaction product thus obtained is purified by electrodialysis. The reaction product is reacted with cetyl alcohol with acid catalysis with camphorsulphonic acid at 90° C. and the butyl alcohol is stripped off under a water-jet vacuum at 90° C. The product is neutralized with NaOH and the product is oxidized to the final product at 60° C. using Adam's catalyst.

PREPARATION EXAMPLE 3

Decyl 2-acetamido-2-deoxy-D-glucopyranoside Uronic Acid Na Salt

Ground chitin is treated at 55° C. with hydrochloric acid and butyl alcohol and the reaction product thus obtained is purified by electrodialysis. The reaction product is reacted with decyl alcohol with acid catalysis with camphorsulphonic acid at 90° C. and the butyl alcohol is stripped off under a water-jet vacuum at 90° C. The product is neutralized with NaOH and the product is oxidized to the final product at 60° C. using Adam's catalyst.

PREPARATION EXAMPLE 4

Dodecyl 2-acetamido-2-deoxy-D-glucopyranoside Uronic Acid Na Salt

Ground chitin is treated at 55° C. with hydrochloric acid and butyl alcohol and the reaction product thus obtained is purified by electrodialysis. The reaction product is reacted with dodecyl alcohol with acid catalysis with camphorsulphonic acid at 90° C. and the butyl alcohol is stripped off under a water-jet vacuum at 90° C. The product is neutralized with NaOH and the product is oxidized to the final product at 60° C. using Adam's catalyst.

PREPARATION EXAMPLE 5

Tetradecyl 2-acetamido-2-deoxy-D-glucopyranoside Uronic Acid Na Salt

Ground chitin is treated at 55° C. with hydrochloric acid and butyl alcohol and the reaction product thus obtained is purified by electrodialysis. The reaction product is reacted with tetradecyl alcohol with acid catalysis with camphorsulphonic acid at 90° C. and the butyl alcohol is stripped off under a water-jet vacuum at 90° C. The product is neutralized with NaOH and the product is oxidized to the final product at 60° C. using Adam's catalyst.

PREPARATION EXAMPLE 6

Palmityl 2-acetamido-2-deoxy-D-glucopyranoside Uronic Acid Na Salt

Ground chitin is treated at 55° C. with hydrochloric acid and butyl alcohol and the reaction product thus obtained is purified by electrodialysis. The reaction product is reacted with palmityl alcohol with acid catalysis with camphorsulphonic acid at 90° C. and the butyl alcohol is stripped off under a water-jet vacuum at 90° C. The product is neutralized with NaOH and the product is oxidized to the final product at 60° C. using Adam's catalyst.

PREPARATION EXAMPLE 7

Eicosyl 2-acetamido-2-deoxy-D-glucopyranoside Uronic Acid Na Salt

Ground chitin is treated at 55° C. with hydrochloric acid and butyl alcohol and the reaction product thus obtained is purified by electrodialysis. The reaction product is reacted with eicosyl alcohol with acid catalysis with camphorsulphonic acid at 90° C. and the butyl alcohol is stripped off under a water-jet vacuum at 90° C. The product is neutralized with NaOH and the product is oxidized to the final product at 60° C. using Adam's catalyst.

EXAMPLE 1

| (O/W emulsion): | % by weight |
|---|---|
| Cetyl 2-acetamido-2-deoxy-D-glucopyranoside uronic acid Na salt | 0.75 |
| Sorbitan stearate | 2.00 |
| Petroleum jelly | 1.0 |
| Paraffin oil, subliquidum | 11.00 |
| Octyldodecanol | 4.00 |
| Hydrogenated coconut fatty acid glycerides | 1.00 |
| Carbomer 2984 | 0.15 |
| Glycerol | 3.00 |
| Sorbitol | 1.00 |
| Panthenol | 1.00 |
| Tocopheryl acetate | 1.25 |
| Bisabolol | 0.10 |
| Perfume, preservative, colourants, antioxidants | q.s. |
| Water | to 100.00 |

EXAMPLE 2

| (W/O emulsion): | % by weight |
|---|---|
| Stearyl 2-acetamido-2-deoxy-D-glucopyranoside uronic acid Na salt | 0.15 |
| PEG-7 hydrogenated castor oil | 4.00 |
| Wool wax alcohol | 1.50 |
| Beeswax | 3.00 |
| Petroleum jelly | 9.00 |
| Ozocerite | 4.00 |
| Paraffin oil, subliquidum | 10.00 |
| Glycerol | 3.00 |
| Sorbitol | 1.00 |
| Panthenol | 1.00 |
| Tocopheryl acetate | 1.25 |
| Bisabolol | 0.10 |
| Magnesium sulphate $7H_2O$ | 0.70 |
| Perfume, preservative, colourants, antioxidants | q.s. |
| Water | to 100.00 |

EXAMPLE 3

| (Hydrodispersion gel): | % by weight |
|---|---|
| Cetyl 2-acetamido-2-deoxy-D-glucopyranoside uronic acid Na salt | 0.25 |
| PEG-8 (polyethylene glycol 400) | 5.00 |
| Ethanol | 2.00 |
| Carbomer 2984 | 0.70 |
| Triglyceride, liquid | 1.50 |
| Glycerol | 4.00 |
| Sorbitol | 1.00 |
| Panthenol | 0.50 |
| Tocopheryl acetate | 0.50 |
| Perfume, preservative, colourants, antioxidants | q.s. |
| Water | to 100.00 |

EXAMPLE 4

| (O/W emulsion): | % by weight |
|---|---|
| Cetyl 2-acetamido-2-deoxy-D-glucopyranoside uronic acid Na salt | 2.00 |
| Glycerol monostearate | 2.00 |
| Petroleum jelly | 1.00 |
| Paraffin oil, subliquidum | 11.00 |
| Octyldodecanol | 4.00 |
| Hydrogenated coconut fatty acid glycerides | 1.00 |
| Carbomer 2984 | 0.15 |
| Glycerol | 3.00 |
| Sorbitol | 1.00 |
| Panthenol | 1.00 |
| Tocopheryl acetate | 1.25 |
| Bisabolol | 0.10 |
| Perfume, preservative, colourants, antioxidants | q.s. |
| Water | to 100.00 |

EXAMPLE 5

| (W/O emulsion): | % by weight |
|---|---|
| Stearyl 2-acetamido-2-deoxy-D-glucopyranoside uronic acid Na salt | 0.25 |
| PEG 7 hydrogenated castor oil | 4.00 |
| Wool wax alcohol | 1.50 |
| Beeswax | 3.00 |
| Petroleum jelly | 9.00 |
| Ozocerite | 4.00 |
| Paraffin oil, subliquidum | 10.00 |
| Glycerol | 3.00 |
| Sorbitol | 1.00 |
| Panthenol | 1.00 |
| Tocopheryl acetate | 1.25 |
| Bisabolol | 0.10 |
| Magnesium sulphate 7 $H_2O$ | 0.70 |
| Perfume, preservative, colourants, antioxidants | q.s. |
| Water | to 100.00 |

EXAMPLE 6

| (Hydrodispersion gel): | % by weight |
|---|---|
| Cetyl 2-acetamido-2-deoxy-D-glucopyranoside uronic acid Na salt | 0.15 |
| PEG 8 (polyethylene glycol 400) | 5.00 |
| Ethanol | 2.00 |
| Carbomer 2984 | 0.70 |
| Triglyceride, liquid | 1.50 |
| Glycerol | 4.00 |
| Sorbitol | 1.00 |
| Panthenol | 0.50 |
| Tocopheryl acetate | 0.50 |
| Perfume, preservative, colourants, antioxidants | q.s. |
| Water | to 100.00 |

EXAMPLE 7

| Shampoo | % by weight |
|---|---|
| Cetyl 2-acetamido-2-deoxy-D-glucopyranoside uronic acid Na salt | 5.00 |
| Sodium lauryl ether sulphate (27.5%) | 25.00 |
| Sodium chloride | q.s. |
| Pearl lustre agent | q.s. |
| Perfume, preservative, colourants, antioxidants | q.s. |
| Water | to 100.00 |

EXAMPLE 8

| Shampoo | % by weight |
|---|---|
| Stearyl 2-acetamido-2-deoxy-D-glucopyranoside uronic acid Na salt | 4.00 |
| Alkylpolyglucose (50%) | 25.00 |
| Sodium chloride | q.s. |
| Pearl lustre agent | q.s. |
| Perfume, preservative, colourants, antioxidants | q.s. |
| Water | to 100.00 |

EXAMPLE 9

| Shampoo | % by weight |
|---|---|
| Stearyl 2-acetamido-2-deoxy-D-glucopyranoside uronic acid Na salt | 5.00 |
| Sodium lauryl ether sulphate (27.5%) | 14.00 |
| Alkylpolyglucose (50%) | 8.00 |
| Sodium chloride | q.s. |
| Pearl lustre agent | q.s. |
| Perfume, preservative, colourants, antioxidants | q.s. |
| Water | to 100.00 |

EXAMPLE 10

| Face cleansing/washing lotion | % by weight |
|---|---|
| Stearyl 2-acetamido-2-deoxy-D-glucopyranoside uronic acid Na salt | 5.00 |
| Sodium cocoamidoacetate (30%) | 10.00 |
| Perfume, preservative, colourants, antioxidants | q.s. |
| Water | to 100.00 |

EXAMPLE 11

| Clear shower bath | % by weight |
|---|---|
| Palmityl 2-acetamido-2-deoxy-D-glucopyranoside uronic acid Na salt | 5.00 |
| Sodium lauryl ether sulphate (27.5%) | 25.00 |
| Alkylpolyglucose (50%) | 4.00 |
| Pearl lustre agent | q.s. |
| Sodium chloride | q.s. |
| Perfume, preservative, colourants, antioxidants | q.s. |
| Water | to 100.00 |

We claim:

1. An alkyl 2-acetamido-2deoxy-D-glucopyranoside uronic acid compound of the formula

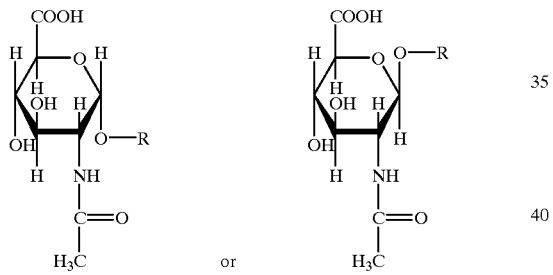

where R represents a branched or unbranched alkyl having from 8 to 48 carbon atoms, or a pharmaceutically or cosmetically acceptable salt of said uronic acid compound.

2. An alkyl 2 acetamido-2-deoxy-D-glucopyranoside uronic acid according to claim 1, wherein R represents an alkyl group having from 10 to 48 carbon atoms.

3. An alkyl 2-acetamido-2-deoxy-D-glucopyranoside uronic acid according claim 1 wherein R represents an alkyl group having from 14 to 22 carbon atoms.

4. An alkyl 2-acetamido-2-deoxy-D-glucopyranoside uronic acid according to claim 1, which is in the form of a salt.

5. An alkyl 2-acetamido-2-deoxy-D-glucopyranoside uronic acid according to claim 4, wherein the salt is selected from the group consisting of alkali metal, ammonium, alkylammonium, dialkylammonium, trialkylammonium and tetraalkylammonium salts.

6. A process for preparing an alkyl 2-acetamido-2-deoxy-D-glucopyranoside uronic acid compound of the formula:

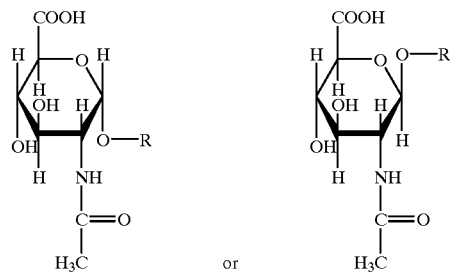

wherein

R represents branched or unbranched alkyl having 8 to 48 carbon atoms;

or a pharmaceutically or cosmetically acceptable salt of said uronic acid compound;

said process comprising:
a) grinding chitin;
b) reacting the ground chitin with an acid and a first aliphatic alcohol having up to 8 carbon atoms, to yield a first reaction product;
c) optionally purifying said first reaction product by dialysis to yield a purified first reaction product;
d) reacting said first reaction product or said purified first reaction with a second aliphatic alcohol having 8 to 48 carbon atoms, wherein said second aliphatic alcohol is different from said first aliphatic alcohol, and said reaction between said first reaction product or said purified first reaction product and said second aliphatic alcohol is under acid catalysis to yield a third reaction product and said first aliphatic alcohol;
e) optionally removing said first aliphatic alcohol by distillation to yield a purer third reaction product; and
f) oxidizing said third reaction product or said purer third reaction product to yield said uronic acid compound.

7. Process according to claim 6, wherein said chitin, in step b) is reacted at 40–70° C.

8. Process according to claim 6, wherein said first reaction product in step c) is purified by electrodialysis.

9. Process according to claim 6, wherein said second aliphatic alcohol in step d) is reacted at 80–100° C.

* * * * *